(12) United States Patent
Fujikura et al.

(10) Patent No.: US 12,259,158 B2
(45) Date of Patent: Mar. 25, 2025

(54) AIR CLEANER

(71) Applicant: KRONGTHIP INC., Tokyo (JP)

(72) Inventors: Kazumi Fujikura, Tokyo (JP); Yoko Shiraishi, Tokyo (JP); Takeshi Hattori, Tokyo (JP)

(73) Assignee: KRONGTHIP INC., Tokyo (JP)

( * ) Notice: Subject to any disclaimer, the term of this patent is extended or adjusted under 35 U.S.C. 154(b) by 171 days.

(21) Appl. No.: 18/019,199

(22) PCT Filed: Jul. 28, 2021

(86) PCT No.: PCT/JP2021/027858
§ 371 (c)(1),
(2) Date: Feb. 1, 2023

(87) PCT Pub. No.: WO2022/030323
PCT Pub. Date: Feb. 10, 2022

(65) Prior Publication Data
US 2023/0280056 A1 Sep. 7, 2023

(30) Foreign Application Priority Data
Aug. 1, 2020 (JP) .................. 2020-131277

(51) Int. Cl.
F24F 8/133 (2021.01)
B01D 47/02 (2006.01)

(52) U.S. Cl.
CPC .............. F24F 8/133 (2021.01); B01D 47/02 (2013.01); B01D 47/024 (2013.01)

(58) Field of Classification Search
CPC ........ F24F 8/133; B01D 47/02; B01D 47/024
See application file for complete search history.

(56) References Cited

U.S. PATENT DOCUMENTS 266,267 A * 10/1882 Breen .................... B01D 47/02
96/336
2,277,566 A * 3/1942 Sprinkle .............. B01D 47/085
261/28
3,063,221 A * 11/1962 Ortgies ................ B01D 47/024
261/78.2
(Continued)

FOREIGN PATENT DOCUMENTS

FR 1421743 A 12/1965
JP H03-217211 A 9/1991
(Continued)

OTHER PUBLICATIONS

Oct. 5, 2021 International Search Report issued in International Patent Application No. PCT/JP2021/027858.
(Continued)

Primary Examiner — Christopher R Zerphey
(74) Attorney, Agent, or Firm — Oliff PLC

(57) ABSTRACT

An air cleaner not susceptible to a decrease in effect. The air cleaner includes: a storage tank that stores a liquid; and an air blowing unit. In the air cleaner, the storage tank has an air receiving region and a dust retention region formed therein, and the air blowing unit blows air to the air receiving region. The dust retention region is a region partitioned by a wall in which an opening is formed toward an upstream side of a flow of the liquid.

2 Claims, 11 Drawing Sheets

(56) References Cited

U.S. PATENT DOCUMENTS

| | | | | | |
|---|---|---|---|---|---|
| 4,585,599 | A | * | 4/1986 | Czarno | B01D 47/024 |
| | | | | | 261/36.1 |
| 5,589,132 | A | * | 12/1996 | Zippel | F24F 6/02 |
| | | | | | 261/92 |
| 6,942,722 | B2 | * | 9/2005 | Braunmiller | F24F 8/125 |
| | | | | | 96/333 |
| 8,758,680 | B2 | * | 6/2014 | Hishida | B01D 47/024 |
| | | | | | 95/218 |

FOREIGN PATENT DOCUMENTS

| | | |
|---|---|---|
| JP | H09-225017 A | 9/1997 |
| JP | 2006-051465 A | 2/2006 |
| JP | 2012-120720 A | 6/2012 |
| KR | 10-2011-0032985 A | 3/2011 |

OTHER PUBLICATIONS

Feb. 7, 2023 International Preliminary Report on Patentability Issued in International Patent Application No. PCT/JP2021/027858.

* cited by examiner

[Figure 1]
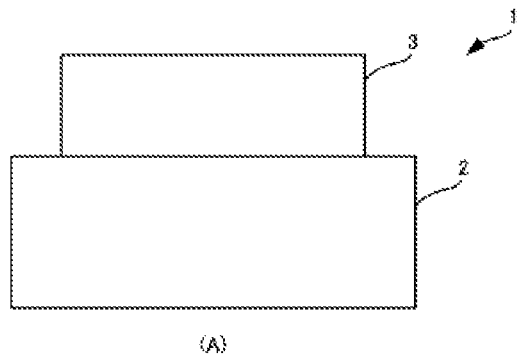
(A)
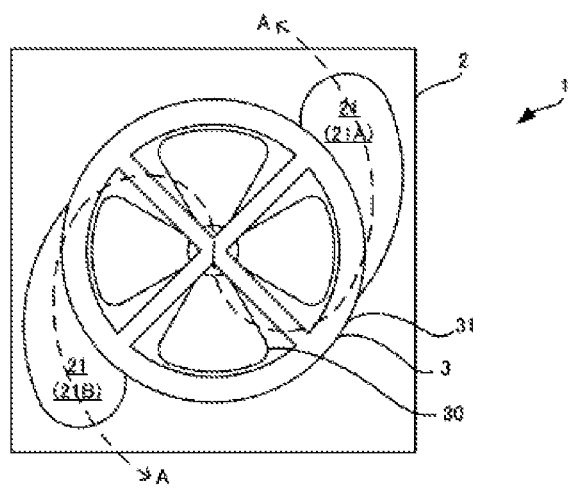
(B)

[Figure 2]
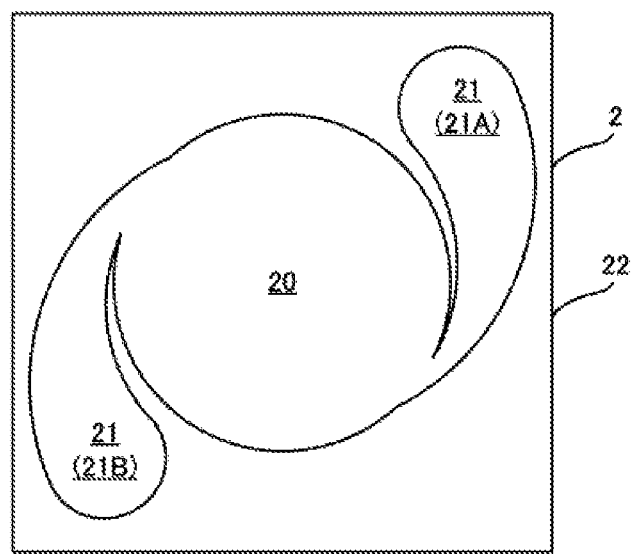

[Figure 3]
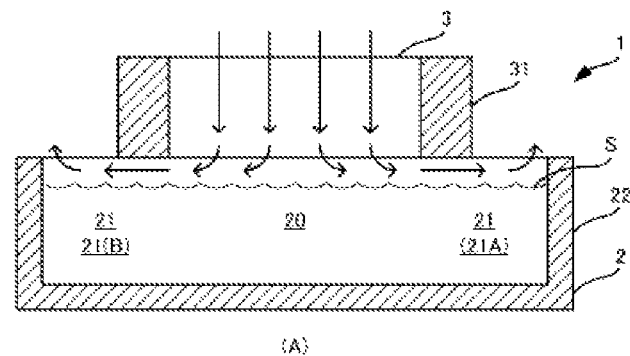
(A)
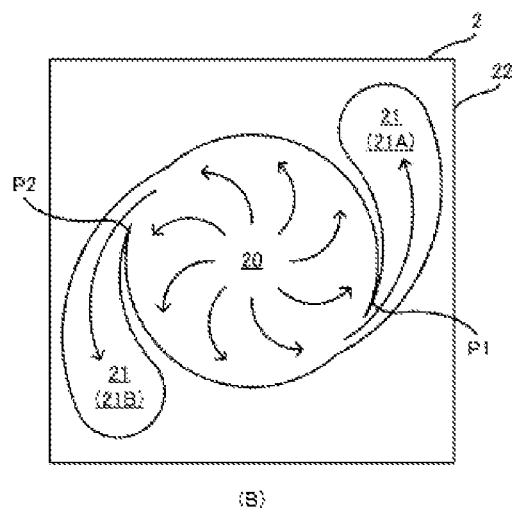
(B)

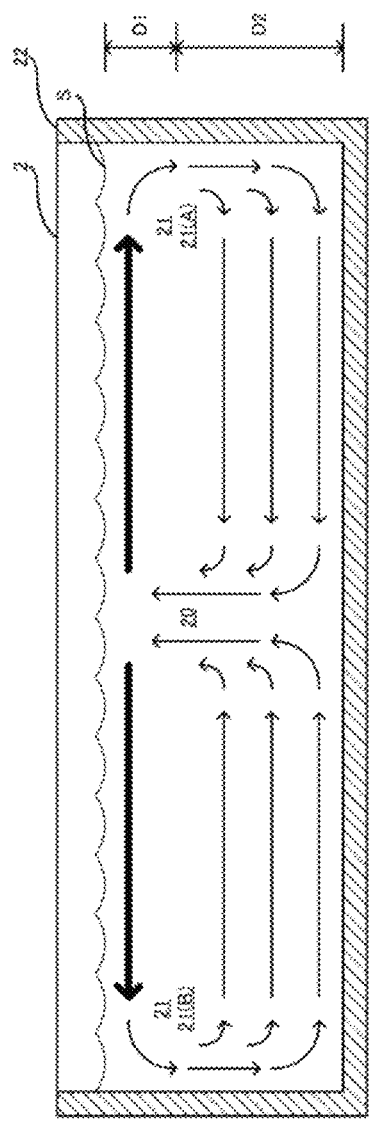
[Figure 4]

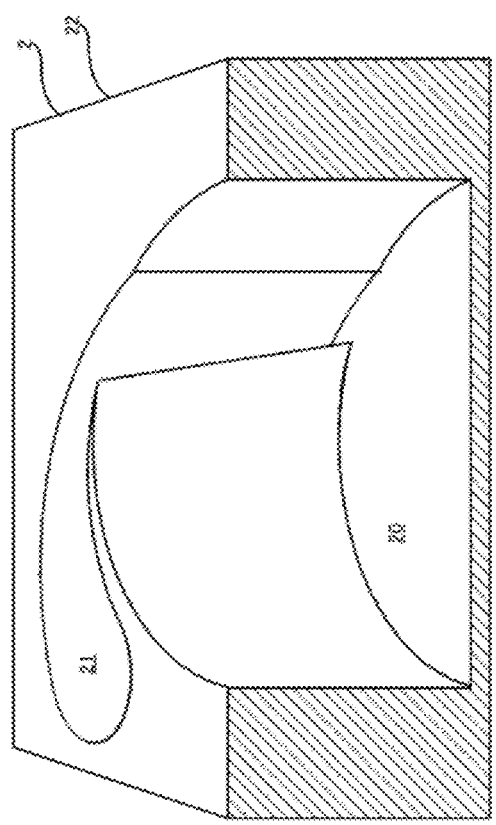
[Figure 5]

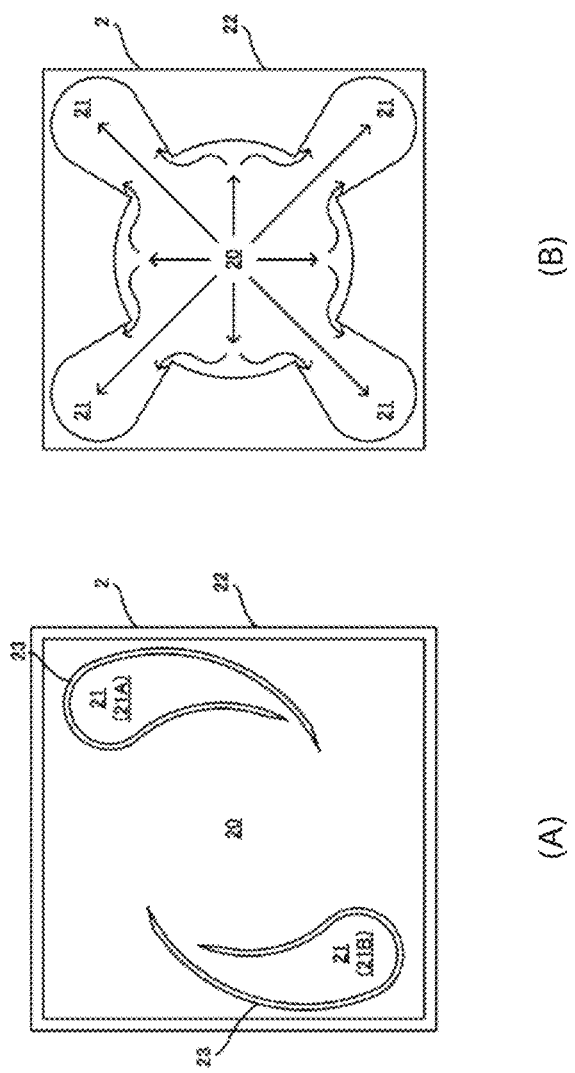

[Figure 7]
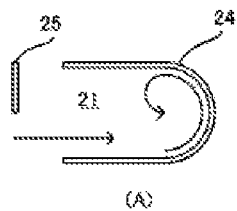
(A)
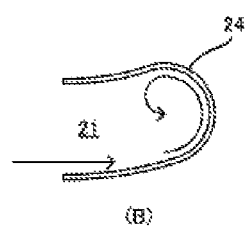
(B)
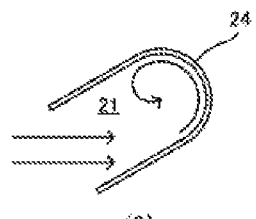
(C)
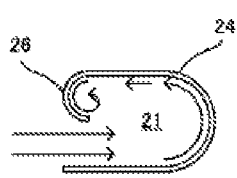
(D)
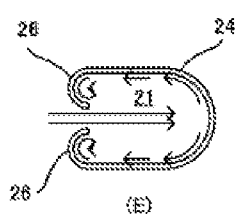
(E)

[Figure 8]
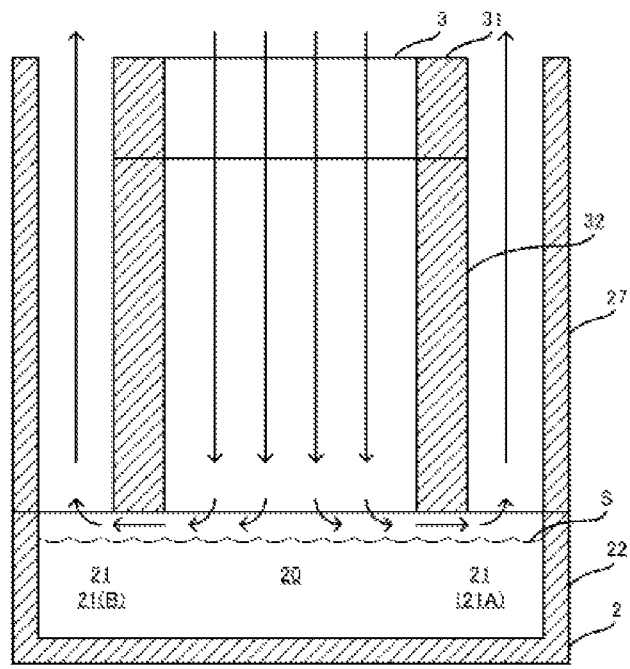

[Figure 9]
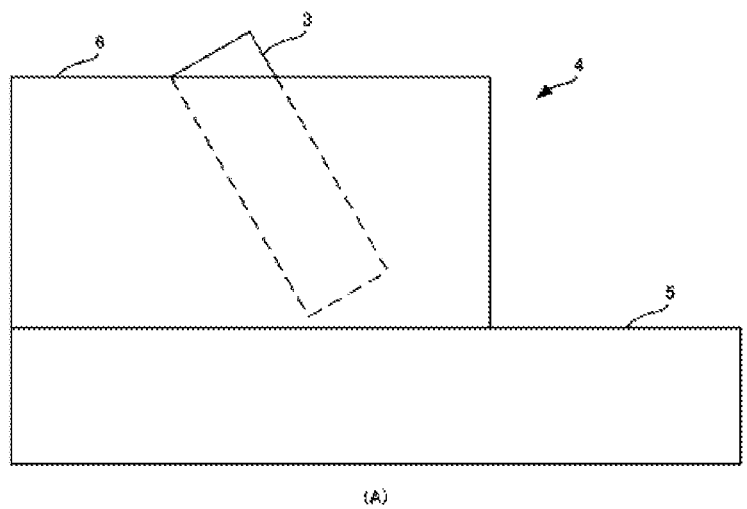
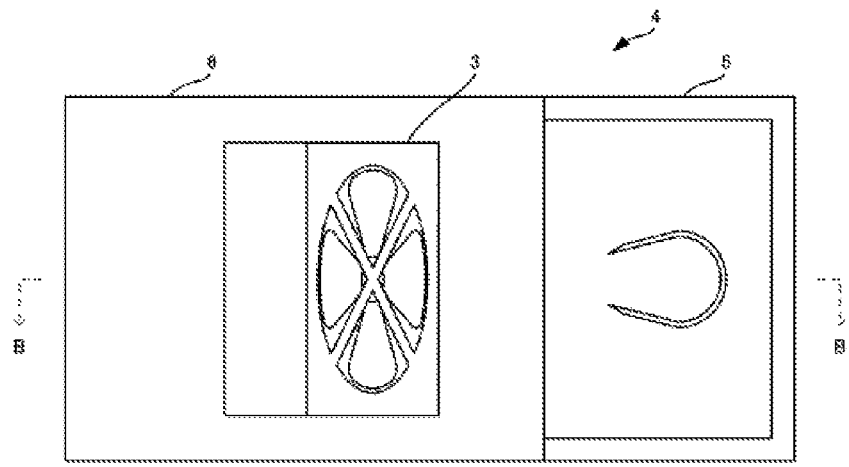

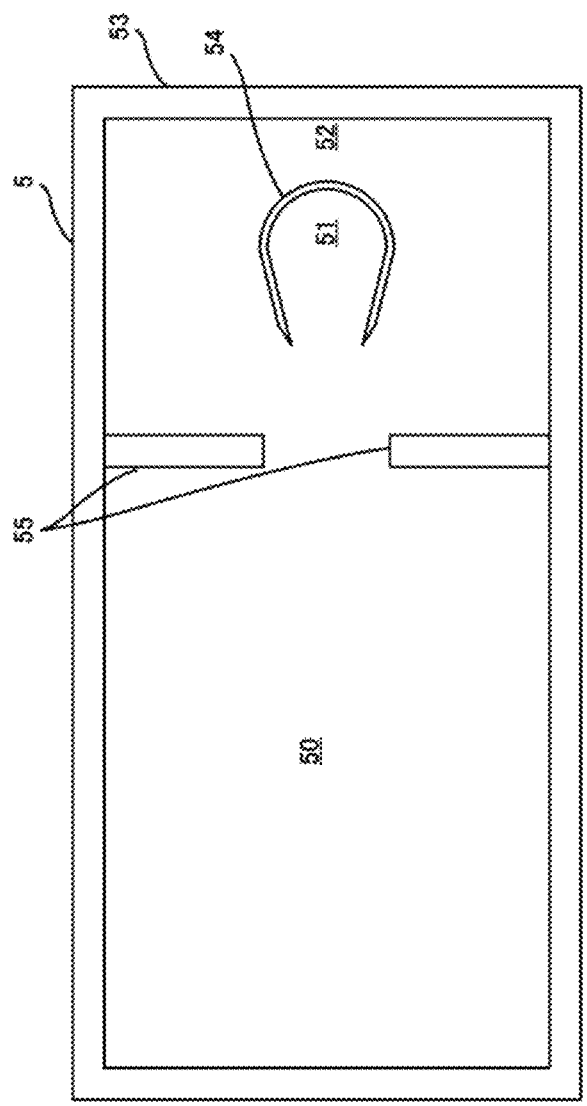
[Figure 10]

[Figure 11]
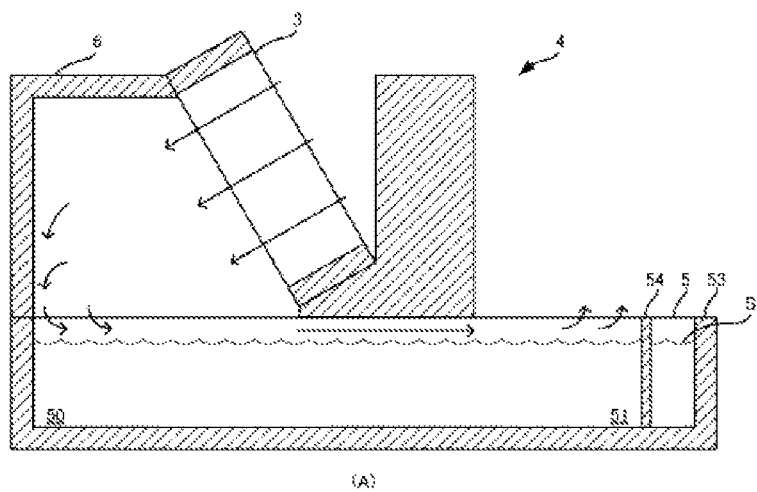
(A)
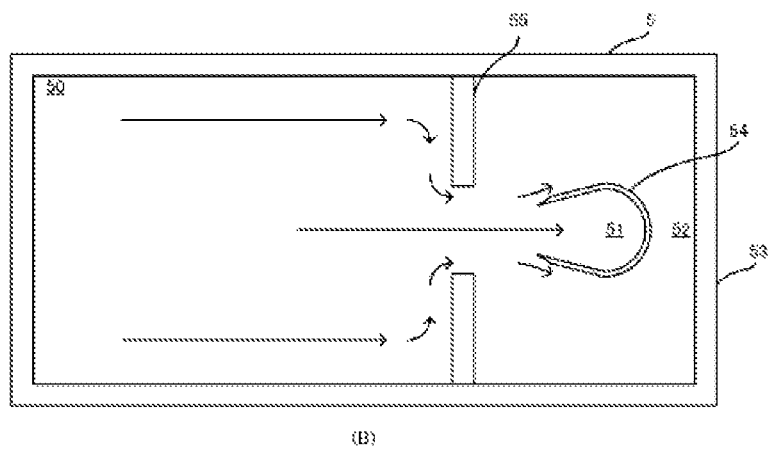
(B)

AIR CLEANER

TECHNICAL FIELD

The present invention relates to an air cleaner for removing dust and bacteria.

BACKGROUND ART

At present, an air cleaner for removing dust and bacteria has been proposed (for example, Patent Literature 1).

CITATION LIST

Patent Literature

Patent Literature 1: JP-A-2012-120720

SUMMARY OF INVENTION

Technical Problem

In the air cleaner described in Patent Literature 1, dust and the like in air are removed by mixing and stirring the air with a liquid. However, in this device, since the liquid used for air cleaning is gradually contaminated, a sufficient effect may not be obtained.

In view of the above-mentioned circumstances, an object of the present invention is to provide an air cleaner not susceptible to a decrease in effect.

Solution to Problem

In order to achieve the above-mentioned object, an air cleaner according to the present invention includes:
 a storage tank that stores a liquid; and
 an air blowing unit, in which
 the storage tank has an air receiving region and a dust retention region formed therein,
 the air blowing unit blows air to the air receiving region, and
 the dust retention region is a region partitioned by a wall in which an opening is formed toward an upstream side of a flow of the liquid.

According to this air cleaner, it is possible to clean the air by causing dust and the like in the air to be contained in the liquid in the air receiving region. In this case, since the dust retention region in which dust and the like in the liquid are likely to be retained is provided, the liquid returning to the air receiving region is less likely to be contaminated, and a cleaning effect can be less likely to be reduced.

In addition, in the air cleaner described above,
 the dust retention region may be a region implemented to have a portion whose width increases as the liquid enters from the opening.

According to this air cleaner, since the liquid entering the dust retention region spreads and the flow of the liquid becomes gentle, dust and the like can be easily retained in the dust retention region In addition, in the air cleaner described above,
 the opening may be narrowed toward a lower side of the storage tank.

According to this air cleaner, an effect of collecting dust and the like by the dust retention region can be expected even when an amount of liquid in the storage tank decreases.

In addition, in the air cleaner described above,
 a portion forming the opening may have an acute angle toward the upstream side of the flow of the liquid.

According to this air cleaner, since the liquid smoothly enters the dust retention region, it is possible to enhance the effect of collecting dust and the like by the dust retention region.

In addition, in the air cleaner described above,
 the dust retention region may include a first dust retention region and a second dust retention region having an opening wider than an opening of the first dust retention region.

According to this air cleaner, the effect of collecting dust and the like by the dust retention region may be enhanced.

In addition, in the air cleaner described above,
 the air blown from the air blowing unit may be discharged through the dust retention region.

According to this air cleaner, the liquid may be fed more reliably to the dust retention region.

In addition, in the air cleaner described above,
 a sub storage tank that stores the liquid is provided, and
 a path through which the air blown from the air blowing unit comes into contact with the liquid stored in the sub storage tank may be provided.

According to this air cleaner, it is possible to further clean or sterilize the air using the liquid in the sub storage tank.

In addition, in the air cleaner described above,
 a vibration applying unit that causes a vibration on a liquid surface of the liquid stored in the storage tank may be provided.

According to this air cleaner, it is possible to expand a contact area between the liquid and the air by causing a vibration on the liquid surface, and it is possible to further enhance the cleaning effect.

Advantageous Effects of Invention

According to the present invention, it is possible to provide an air cleaner not susceptible to a decrease in effect.

BRIEF DESCRIPTION OF DRAWINGS

FIG. 1 is a view illustrating a first embodiment of an air cleaner of the present invention;

FIG. 2 is a view illustrating a storage tank 2 of an air cleaner 1 according to the first embodiment;

FIG. 3(A) is a view illustrating flows of air from an air blower 3, and FIG. 3(B) is a view illustrating flows generated on a liquid surface of the storage tank 2;

FIG. 4 is a view illustrating flows of the liquid inside the storage tank 2;

FIG. 5 is a cross-sectional perspective view illustrating an example of a configuration applicable to the storage tank 2;

FIG. 6 is a view illustrating an example of a configuration applicable to the first embodiment;

FIG. 7 is a view illustrating an example of a configuration applicable to the first embodiment;

FIG. 8 is a cross-sectional view illustrating a modification of the first embodiment;

FIG. 9 is a view illustrating a second embodiment of the air cleaner of the present invention;

FIG. 10 is a view illustrating a storage tank 5 of an air cleaner 4 according to the second embodiment; and FIG. 11(A) is a view illustrating flows of air from the air blower 3, and FIG. 11(B) is a view illustrating flows generated on a liquid surface of the storage tank 5.

DESCRIPTION OF EMBODIMENTS

Hereinafter, an air cleaner of the present invention will be described with reference to the drawings.

First Embodiment

Hereinafter, an example of an embodiment of an air cleaner of the present invention will be described with reference to FIG. 1. FIG. 1(A) is a front view illustrating a first embodiment of the air cleaner of the present invention, and FIG. 1(B) is a plan view illustrating the first embodiment.

As illustrated in FIG. 1, an air cleaner 1 according to the first embodiment includes a storage tank 2 that stores a liquid, and an air blower 3 provided above the storage tank 2. In the air blower 3, a blade member 30 including four blades is rotationally driven by a motor (not illustrated) in a state where the blade member 30 is supported in an inner space of an outer frame 31, and air is blown toward the storage tank 2. FIG. 2 is a plan view illustrating the storage tank 2 (a view in which the air blower 3 is removed from FIG. 1(B)). As illustrated in FIG. 2, a central region 20 (hereinafter, referred to as an air receiving region 20) and two regions 21 (hereinafter, referred to as dust retention regions 21) connected to the air receiving region 20 are formed by an outer frame 22 in the storage tank 2 as regions that store the liquid. Among these, the air receiving region 20 is a region having the same size as an air blowing range from the air blower 3 (path in an inner space of the outer frame 31), and as illustrated in FIG. 1(B), an entire range of the air receiving region 20 is covered by the air blower 3. On the other hand, the dust retention regions 21 are located outside the air receiving region 20 and outside the air blowing range of the air blower 3 (path in the inner space of the outer frame 31), and as illustrated in FIG. 1(B), a part of the dust retention region 21 is covered by the outer frame 31 of the air blower 3.

The air cleaner 1 according to the first embodiment removes dust and the like by bringing the air blown from the air blower 3 into contact with the liquid in the storage tank 2, cleans the air, and then discharges the cleaned air. Hereinafter, this operation will be described with reference to FIGS. 3 and 4. FIG. 3(A) is a view illustrating flows of the air blown from the air blower 3 in a cross section taken along a line A-A of FIG. 1(B), and FIG. 3(B) is a view illustrating flows generated on a liquid surface of the storage tank 2 by the air blown from the air blower 3. In the cross-sectional view of FIG. 3(A), the blade member 30 is not illustrated. In the same drawing, the outer frame 31 of the air blower 3 and the outer frame 22 of the storage tank 2 are each indicated by leftward descending hatching. In addition, a liquid surface S of the liquid stored in the storage tank 2 is indicated by a wavy line. FIG. 4 is a view illustrating flows of the liquid inside the storage tank 2.

As described above, in the storage tank 2, the air receiving region 20 has a size corresponding to the air blowing range from the air blower 3 (path in the inner space of the outer frame 31), and the air blown from the air blower 3 advances while rotating counterclockwise with respect to the liquid surface S of the air receiving region 20. Air applied to the liquid surface S of the air receiving region 20 passes between the outer frame 31 of the air blower 3 and the liquid surface S of the liquid stored in the storage tank 2, reaches the dust retention regions 21, and is then discharged. In FIG. 3(A), a series of flows of the air are indicated by arrows.

By the flows described above, dust in the air can be brought into contact with the liquid in the storage tank 2 and entrained into the liquid. In addition, for example, a contaminant such as formaldehyde known as a causative substance of sick house syndrome can also be entrained into the liquid. Further, viruses and bacteria can also be entrained into the liquid or can be destroyed by impinging upon the liquid. As described above, the air blown from the air blower 3 can be cleaned. As the liquid in the storage tank 2, in addition to a liquid such as water, liquid silicon, and slightly acidic electrolyzed water, a liquid to which an additive is added, such as sterilizing water in which a fired powder of a scallop shell is dissolved, or a liquid in which a surfactant such as soap or detergent is dissolved in water may be used.

Next, the flow of the liquid in the storage tank 2, which is generated by the flow of the air described above, will be described. The air from the air blower 3 flows toward the dust retention region 21 while rotating counterclockwise from the air receiving region 20, and along with this flow, a flow of the liquid flowing toward the dust retention region 21 while rotating counterclockwise from the air receiving region 20 is generated also on the liquid surface of the storage tank 2. In FIG. 3(B), the flows of the liquid on the liquid surface are indicated by arrows. The dust retention region 21 is a region implemented such that the liquid enters along the flow on the liquid surface, and is a region partitioned by a wall (the outer frame 22 in the storage tank 2) in which an opening is formed toward the upstream side of the flow of the liquid.

Further, since the flow of the liquid on the liquid surface of the storage tank 2 is generated by the flows described above, the liquid circulates inside the storage tank 2 through a path as illustrated in FIG. 4. First, on the liquid surface, the liquid that has been driven from the air receiving region 20 to the dust retention regions 21 collides with the outer frame 22 at the innermost portion and descends. Then, on a bottom portion side of the storage tank 2, flows from the dust retention regions 21 toward the air receiving region 20 are formed by the descended liquid. Further, the liquid that has returned to the air receiving region 20 rises to the liquid surface, and circulates again by being pushed away from the air receiving region 20 to the dust retention regions 21 by the flows of the air.

In the above-mentioned circulation, the flows of the liquid from the air receiving region 20 to the dust retention regions 21 are generated in the vicinity of the liquid surface (range of D1 illustrated in FIG. 4), whereas the flows returning from the dust retention regions 21 to the air receiving region 20 may be generated in a range (range of D2 illustrated in FIG. 4) excluding the vicinity of the liquid surface. As the water depth increases, the range (range of D2 illustrated in FIG. 4) in which the returning flows are generated becomes larger, and a speed of the flows returning from the dust retention regions 21 to the air receiving region 20 becomes slower. That is, the liquid can be driven from the air receiving region 20 to the dust retention regions 21 with a fast flow, and the liquid can be returned from the dust retention regions 21 to the air receiving region 20 with a slow flow. In FIG. 4, a difference in speed of the flows is indicated by a difference in thickness of the arrows.

As described above, in the air cleaner 1 according to the first embodiment, dust and the like in the air can be entrained into the liquid in the storage tank 2 to clean the air. Dust and the like entrained into the liquid are driven from the air receiving region 20 toward the dust retention regions 21, and dust and the like descending and precipitated as the liquid descends are retained in the dust retention regions 21 and less likely to be returned to the air receiving region 20, so that the liquid used for cleaning the air (liquid in the vicinity of the liquid surface in contact with the air) can be less likely to be contaminated. As an installation position of the dust retention region 21, the dust retention region 21 is not limited to a configuration directly connected to the air receiving region 20, and may be a configuration indirectly connected to the air receiving region 20 via another region provided therebetween. In any case, any configuration may be used as long as the liquid from the air receiving region 20 reaches the dust retention region 21. That is, the dust retention region 21 may be a region partitioned by a wall in which an opening is formed toward an upstream side of a flow of the liquid. In addition, the number of the dust retention region 21 is not particularly limited, and for example, a configuration in which only one dust retention region 21 is provided may be used.

When the liquid is driven from the air receiving region 20 to the dust retention region 21, a wave is generated on the liquid surface by the flow of the air, and fine waves are further generated by interference of the wave with the dust retention region 21. Here, in a state where dust and the like do not completely conform to the liquid and adhere to the liquid while enclosing the air, it is considered that dust and the like may not descend in the liquid or may float even once they descend, but since dust and the like vibrate due to the fine waves generated in the dust retention region 21 and conform to the liquid, dust and the like can be retained in the dust retention region 21 more reliably. Further, since the dust retention region 21 is less likely to be affected by a water flow other than that illustrated in FIG. 4, it is possible to prevent dust and the like retained in the dust retention region 21 from being scattered.

In addition, as illustrated in FIG. 3(B), the dust retention region 21 is implemented to have a portion whose width increases as the liquid enters. According to this configuration, since the liquid entered the dust retention region 21 spreads and the flow of the liquid becomes gentle, dust and the like can be easily retained in the dust retention region 21.

In addition, as illustrated in FIG. 3(B), a portion (see reference numerals P1 and P2) forming the opening of the dust retention region 21 has an acute angle toward the upstream side of the flow of the liquid. According to this configuration, since the liquid smoothly enters the dust retention region 21, it is possible to enhance the effect of collecting dust and the like by the dust retention region 21.

In addition, as illustrated in FIG. 2, the storage tank 2 is provided with two dust retention regions 21A and 21B (hereinafter, referred to as a first dust retention region 21A and a second dust retention region 21B, respectively). When the first dust retention region 21A and the second dust retention region 21B are compared, an opening of the second dust retention region 21B is wider than an opening of the first dust retention region 21A. In experiments conducted by the inventors, since an amount of dust retained in the dust retention region 21 changes depending on an amount of liquid and a flow velocity of the storage tank 2, it is considered that a shape and a size of the dust retention region 21 may be appropriate in accordance with the amount and the flow velocity of the liquid. However, the situation is always changed, such as the amount of liquid in the storage tank 2 is reduced due to evaporation or the like. The air cleaner 1 according to the first embodiment adopts a configuration in which a plurality of dust retention regions 21 having different opening widths are provided so as to cope with such a change. According to this configuration, as compared with a case where one dust retention region 21 is provided or a case where a plurality of dust retention regions 21 having the same opening width are provided, the effect of collecting dust and the like by the dust retention region 21 may be enhanced.

In addition, in the air cleaner 1 according to the first embodiment, as illustrated in FIG. 5 (cross-sectional perspective view of the storage tank 2), the opening of the dust retention region 21 may be implemented to be narrowed toward the lower side of the storage tank 2. In the experiments conducted by the inventors, when the opening is narrowed in a case where the amount of liquid in the storage tank 2 is small, dust and the like are collected more than in a case where the opening is not narrowed, and thus, by adopting this configuration, the effect of collecting dust and the like by the dust retention region 21 can be expected even when the amount of liquid in the storage tank 2 decreases.

In the air cleaner 1 according to the first embodiment described above, the dust retention region 21 is formed by the outer frame 22 of the storage tank 2, but the dust retention region 21 is not limited to this configuration, and may be formed using a partition wall 23 different from the outer frame 22, for example, as illustrated in FIG. 6(A). The dust retention region 21 may be a region partitioned by a wall in which an opening is formed toward the upstream side of the flow of the liquid such that the liquid enters along the flow generated on the liquid surface of the storage tank 2, and may be a region in which the flow on the liquid surface entered the region collides with the wall. In particular, in the air cleaner 1 according to the first embodiment, the dust retention region 21 is formed along the flow of the air after the air is applied to the air receiving region 20, and in this way, the liquid can easily enter the liquid surface.

In the air cleaner 1 according to the first embodiment described above, a configuration in which the air blower 3 is disposed directly above the storage tank 2 is used, but the air cleaner 1 is not limited to this configuration, and may have a configuration in which air is blown through a duct, for example. In addition, the air blower 3 according to the first embodiment is implemented such that the blown air rotates in a spiral form, but a configuration such as a sirocco fan may be used. In addition, the number of blades is also not limited. That is, the configuration of the air blower 3 is not limited as long as it is an air blowing unit for applying air to the liquid surface of the storage tank 2. In the air cleaner 1 according to the first embodiment, it is disclosed that the air from the air blower 3 rotates in a spiral form, but in a case where the air from the air blower 3 travels straightly without rotating, the flow on the liquid surface to the dust retention region 21 is not successfully generated in the configuration of the storage tank 2 described above. In such a case, in consideration of an actual flow of the liquid, the air receiving region 20 and the dust retention region 21 may be shaped as illustrated in FIG. 6(B).

In some cases, a vortex is generated in the liquid surface depending on a speed and a direction of the flow on the liquid surface entering the dust retention region 21, an angle at which the wall forming the dust retention region 21 and the flow on the liquid surface collide with each other, and the like, and descending of the liquid and the dust and the like contained therein is further promoted. Hereinafter, an example of such a configuration will be described with reference to FIG. 7. FIG. 7 is a view illustrating flows on the liquid surface using a partition wall 24 forming the dust retention region 21 and modifications thereof. In FIG. 7, in order to describe a deformable configuration in an easy-to-understand manner, the partition wall 24 having a shape different from those of the outer frame 22 of FIG. 2 and the partition wall 23 of FIG. 6(A) is used.

FIG. 7(A) illustrates an example in which the flow on the liquid surface entering the dust retention region 21 is biased to one side of the partition wall 24 by a wall 25 provided so as to partially shield the flow on the liquid surface entering the dust retention region 21, and the flow on the liquid surface swirls along the partition wall 24 and a vortex is generated. The wall 25 that shields the flow on the liquid surface directly acts on the flow on the liquid surface, and such a wall may be provided in a discharge path of the air from the air blower 3. That is, the flow of the air from the air blower 3 is biased to one side of the partition wall 24 of the dust retention region 21, so that the flow on the liquid surface entering the dust retention region 21 can be biased to the one side of the partition wall 24.

FIG. 7(B) illustrates an example in which a shape of the partition wall 24 is curved, so that the flow on the liquid surface swirls along the partition wall 24 and a vortex is generated.

FIG. 7(C) illustrates an example in which an orientation of the partition wall 24 is inclined with respect to the flow on the liquid surface as compared with that in FIG. 6(A). In this example, the flow on the liquid surface obliquely collides with the partition wall 24 before reaching an inner part of the dust retention region 21, and the flow on the liquid surface swirls along the partition wall 24 and a vortex is generated.

FIG. 7(D) illustrates an example in which a barb 26 is provided in an opening portion of the partition wall 24. In the example of FIG. 7(A), there is a possibility that the flow on the liquid surface returns to an opening side, and according to this configuration, a vortex is likely to be generated also with respect to the flow on the liquid surface returned to the opening side, allowing the liquid to descend more reliably in the dust retention region 21. In FIG. 7(D), the barb 26 is provided on one side of the opening portion of the partition wall 24, but as illustrated in FIG. 7(E), the barb 26 may be provided on both sides of the opening portion of the partition wall 24.

In addition, in order to prevent dust and the like precipitated in the dust retention region 21 from scattering, a configuration in which the water depth on an inner side is deeper than the water depth on a front side (opening side) may be used.

In the air cleaner 1 according to the first embodiment, air is sucked from the air blower 3 and discharged from between the liquid surface of the dust retention region 21 of the storage tank 2 and the outer frame 31 of the air blower 3, but in this configuration, a region for air discharge is narrower than a region for air suction. When such a configuration is adopted, a momentum of the air discharge is maintained, and the flow on the liquid surface entering the dust retention region 21 can be made more reliable.

In the air cleaner 1 according to the first embodiment, the air is blown from directly above the liquid surface, but an orientation of the air blowing is not limited to the configuration in which the air is blown from directly above the liquid surface as described in a second embodiment to be described later.

In addition to the above-mentioned configuration, a sub storage tank that stores a liquid having a sterilization effect (for example, hypochlorous acid water) may be provided separately from the storage tank 2, and air purified by the storage tank 2 may be discharged after being exposed to the liquid in the sub storage tank.

In addition to the above-mentioned configuration, a configuration for causing a vibration on the liquid surface of the storage tank 2 may be added. According to this configuration, since waves and air bubbles are generated due to the vibration on the liquid surface and an area in contact with the air is increased, purification performance can be enhanced. In the air cleaner 1 according to the first embodiment, since a vibration of the air blower 3 is transmitted to the storage tank 2, the air blower 3 is implemented to cause a vibration on the liquid surface of the storage tank 2. In addition, a sound generated from the air blower 3 is also one form of a configuration for causing a vibration on the liquid surface of the storage tank 2. More specifically, the sound generated from the air blower 3 in a space between the air blower 3 and the liquid surface of the storage tank 2 is echoed, and the echoed sound causes a vibration on the liquid surface. As described above, in the first embodiment, the air blowing unit is integrated with the configuration that causes a vibration on the liquid surface, but respective configurations thereof may be individually provided. In addition, in order to cause a vibration on the liquid surface of the storage tank 2, a vibrating member may be provided on the liquid surface or in the liquid to directly cause a vibration on the liquid surface. In addition to such a configuration, a configuration may be used in which, for example, a turbulent flow generation unit that generates a turbulent flow is provided in a passage of the air from the air blower 3, and a vibration may be caused on the liquid surface using a vibration generated by the turbulent flow. That is, the air blowing unit is not limited to the configuration according to the first embodiment as long as a vibration is caused on the liquid surface of the storage tank 2.

In the air cleaner 1 according to the first embodiment, the air blown from the air blower 3 is brought into contact with the liquid in the storage tank 2 to clean the air. Here, a configuration may be used in which a flow path of the air is further formed so as to increase the contact area between the air and the liquid, the liquid supplied from the storage tank 2 is caused to flow on a surface forming the flow path, and the liquid is returned to the storage tank 2. In addition, the air cleaner 1 is not limited to the configuration in which the liquid is caused to flow on the surface forming the flow path, and a configuration in which the liquid supplied from the storage tank 2 is dispersed in the flow path may be used. FIG. 8 illustrates an example in which a cylindrical member 32 is provided between the air blower 3 and the storage tank 2 in FIG. 3(A), and a frame member 27 extending above the outer frame 22 of the storage tank 2 is further provided, thereby forming such a flow path of the air. In such a configuration, by causing the liquid to flow (or be dispersed) in the flow path, the air passing through the flow path can be cleaned, and the performance of the air cleaner 1 can be enhanced.

Second Embodiment

Hereinafter, an example of an embodiment of the air cleaner of the present invention will be described with reference to FIG. 9. FIG. 9(A) is a side view illustrating a second embodiment of the air cleaner of the present invention, and FIG. 9(B) is a plan view illustrating the second embodiment.

As illustrated in FIG. 9, an air cleaner 4 according to the second embodiment includes a storage tank 5 that stores a liquid, and an air blowing box 6 provided above the storage tank 5. The air blowing box 6 has a configuration in which the air blower 3 according to the first embodiment is obliquely disposed and a bottom portion thereof is opened, and blows outside air toward the inside (liquid surface of the storage tank 5). FIG. 10 is a plan view illustrating the storage tank 5 (a view in which the air blowing box 6 is removed from FIG. 9(B)). As illustrated in FIG. 10, in the storage tank 5, a widest region 50 (hereinafter, referred to as a first region 50), the first region 50 thereof, and a region 52 (hereinafter, referred to as a second region 52) are formed by a wall 55 having a hole and an outer frame 53 as regions that store the liquid. Further, in the second region 52, a region 51 (hereinafter, referred to as a third region 51) is formed by a partition wall 54. Among these, the first region 50 is in a state where an entire range of the first region 50 is covered by the air blowing box 6 as illustrated in FIG. 9(B). On the other hand, the third region 51 is located outside the first region 50 and outside an air blowing range of the air blowing box 6.

The air cleaner 4 according to the second embodiment removes dust and the like by bringing the air blown from the air blower 3 of the air blowing box 6 into contact with the liquid in the storage tank 5, cleans the air, and then discharges the air. Hereinafter, this operation will be described with reference to FIG. 11. FIG. 11(A) is a view illustrating flows of the air blown from the air blower 3 in a cross section taken along a line B-B of FIG. 9(B), and FIG. 11(B) is a view illustrating a flow generated on the liquid surface of the storage tank 5 by the air blown from the air blower 3. In the cross-sectional view of FIG. 11(A), the blade member 30 is not illustrated. In the same drawing, the air blowing box 6, the outer frame 31 of the air blower 3, the outer frame 53 of the storage tank 5, and the partition wall 54 are each indicated by leftward descending hatching. In addition, a liquid surface S of the liquid stored in the storage tank 5 is indicated by a wavy line.

As described above, in the storage tank 5, the first region 50 is covered with the air blowing box 6, and the air blown from the air blower 3 of the air blowing box 6 is applied to the liquid surface S of the first region 50. According to the second embodiment, the air blower 3 is obliquely disposed, and the air blown from the air blower 3 is applied to an end of the first region. The air applied to the liquid surface S of the first region 50 passes between a bottom portion of the air blowing box 6 and the liquid surface S of the liquid stored in the storage tank 5, reaches the third region 51, and is then discharged. In FIG. 11(A), a series of flows of the air are indicated by arrows. By the flows described above, the air blown from the air blower 3 can be cleaned by the same operation as that of the air cleaner 1 according to the first embodiment.

Next, the flow of the liquid in the storage tank 5, which is generated by the flow of the air described above, will be described. The air from the air blower 3 flows from the first region 50 toward the third region 51, and along with this flow, a flow from the first region 50 to the third region 51 is generated also in the liquid surface of the storage tank 5. In FIG. 11(B), the flow on the liquid surface is indicated by an arrow. In a region to which the air from the air blower 3 is directly applied, since air flows are complicated, a path thereof is not determined to be one, but finally, the flow from the first region 50 to the third region 51 is generated.

Since a flow is generated on the liquid surface of the storage tank 5 due to the flow described above, the liquid circulates inside the storage tank 5 in a flow similar to that in the path described in FIG. 4. First, on the liquid surface, the liquid that has been driven from the first region 50 to the third region 51 collides with the partition wall 54 and descends. Then, a flow from the third region 51 toward an end of the first region 50 is formed on a bottom portion side of the storage tank 5 by the descended liquid, and a liquid that has returned to the end of the first region 50 rises to the liquid surface, and is pushed away from the first region 50 to the third region 51 by the flow of the air again.

As described above, the air cleaner 4 according to the second embodiment also achieves an effect similar to that of the air cleaner 1 according to the first embodiment. That is, dust and the like in the air can be entrained into the liquid in the storage tank 5 to clean the air, the liquid in the vicinity of the liquid surface in contact with the air can be made less likely to be contaminated, and further, the dust and the like precipitated in an inner part of the third region 51 can be prevented from being scattered. Other configurations applicable to the first embodiment can also be applied to the second embodiment. In this case, the configuration of the dust retention region 21 according to the first embodiment can be applied to the third region 51 according to the second embodiment, and the configuration of the air receiving region 20 according to the first embodiment can be applied to the first region 50 according to the second embodiment.

REFERENCE SIGNS LIST 1, 4 Air cleaner
2, 5 Storage tank
3 Air blower
6 Air blowing box

The invention claimed is:

1. An air cleaner, comprising:
a storage tank configured to store a liquid; and
an air blower, wherein
the storage tank has an air receiving region and a dust retention region formed therein,
the air blower is configured to blow air to the air receiving region,
the dust retention region is a region partitioned by a wall in which an opening is formed toward an upstream side of a flow of the liquid, and
a bottom of the wall extends farther in a circumferential direction than does a top of the wall.

2. An air cleaner, comprising:
a storage tank configured to store a liquid; and
an air blower, wherein
the storage tank has an air receiving region and a dust retention region formed therein,
the air blower is configured to blow air to the air receiving region, and
the dust retention region is a region partitioned by a wall in which an opening is formed toward an upstream side of a flow of the liquid, wherein
an edge of the wall extends at an acute angle from a bottom surface of the wall.

* * * * *